(12) United States Patent
Prugue et al.

(10) Patent No.: US 10,670,882 B2
(45) Date of Patent: Jun. 2, 2020

(54) INTERPOSED GOGGLE FRAME SNAP ASSEMBLY

(71) Applicant: Bell Sports, Inc., Scotts Valley, CA (US)

(72) Inventors: Ximena Prugue, Santa Cruz, CA (US); Michael J. Musal, Soquel, CA (US)

(73) Assignee: Bell Sports, Inc., Scotts Valley, CA (US)

( * ) Notice: Subject to any disclaimer, the term of this patent is extended or adjusted under 35 U.S.C. 154(b) by 78 days.

(21) Appl. No.: 15/814,239

(22) Filed: Nov. 15, 2017

(65) Prior Publication Data

US 2018/0136484 A1    May 17, 2018

Related U.S. Application Data

(60) Provisional application No. 62/422,414, filed on Nov. 15, 2016.

(51) Int. Cl.
    *G02C 1/06*     (2006.01)
    *A61F 9/02*     (2006.01)
    (Continued)

(52) U.S. Cl.
    CPC ............... *G02C 1/06* (2013.01); *A61F 9/025* (2013.01); *G02C 3/003* (2013.01); *G02C 5/008* (2013.01);
    (Continued)

(58) Field of Classification Search
    CPC ........ G02C 1/06; G02C 2200/08; G02C 1/04; G02C 11/08; G02C 1/02; G02C 1/10; G02C 5/008; G02C 5/02; G02C 5/10; G02C 2200/02; G02C 5/00; G02C 9/00; G02C 1/08; G02C 2200/04; G02C 2200/12; G02C 3/003; G02C 5/2272; G02C 11/02; G02C 1/00; G02C 2200/06
    See application file for complete search history.

(56) References Cited

U.S. PATENT DOCUMENTS 5,685,022 A  * 11/1997  Essman ............... A61F 9/025
                                                        2/434
2004/0025232 A1 * 2/2004  Hartley ............... A61F 9/022
                                                        2/452

(Continued)

FOREIGN PATENT DOCUMENTS

WO        2013003776        1/2001

*Primary Examiner* — William R Alexander
*Assistant Examiner* — Sharrief I Broome
(74) *Attorney, Agent, or Firm* — Amardeep S. Grewal; Gerard M. Donovan; Reed Smith LLP (57) ABSTRACT

A pair of goggles with a lens assembly, a goggle frame, and at least one lens retention shelf is disclosed. The lens assembly includes a lens with a projection extending from the assembly. The goggle frame is made of a first material and has a frame aperture sized large enough to receive the projection from the lens assembly through it. The lens retention shelf is made of a second material harder than the first material and is disposed behind the frame. The first lens retention shelf includes a projection connector corresponding to the projection, the projection connector is aligned with the frame aperture and sized sized to receive and engage the projection with the goggle frame interposed between the lens retention shelf and the lens.

19 Claims, 8 Drawing Sheets

(51) Int. Cl.
*G02C 3/00* (2006.01)
*G02C 5/00* (2006.01)

(52) U.S. Cl.
CPC ..... *G02C 2200/02* (2013.01); *G02C 2200/08* (2013.01)

(56) References Cited

U.S. PATENT DOCUMENTS

2012/0137414 A1* 6/2012 Saylor ................ A61F 9/025
2/435
2013/0222213 A1 8/2013 Abdollahi et al.
2014/0232980 A1* 8/2014 Harms ................ G02C 11/00
351/158

* cited by examiner

INTERPOSED GOGGLE FRAME SNAP ASSEMBLY

RELATED APPLICATIONS

This application is based on, claims priority to, and incorporates herein by reference in its entirety, U.S. Provisional Patent Application Ser. No. 62/422,414, filed on Nov. 15, 2016, and entitled "INTERPOSED GOGGLE FRAME SNAP ASSEMBLY."

TECHNICAL FIELD

Aspects of this document relate generally to goggles, and more specifically to goggles and methods of assembling a pair of goggles.

BACKGROUND

Goggles are desirable to have a soft, flexible goggle frame, for the purpose of comfort and a good fit of the goggle frame to the wearer's face. Goggles with interchangeable lenses have been known to include a lens with a series of projections extending from the lens assembly to engage in a series of corresponding holes on the goggle frame. The flexibleness of the goggle frame causes the holes on the goggle frame also flexible and lack of a sufficient grip to hold the projections in the holes. As a result, the projections on the lenses become detached from the holes and the goggles become dissembled.

SUMMARY

According to an aspect of the disclosure, a pair of goggles may comprise a lens assembly, a goggle frame, first and second lens retention shelves, and a goggle strap. The lens assembly may include at least one lens carrier comprising a first carrier side, a second carrier side opposite the first carrier side, and at least one projection disposed on each of the first and second carrier sides, and at least one lens mounted on the lens carrier. The goggle frame may comprise a first frame side and a second frame side opposite the first frame side. The goggle frame may comprise a first material. Each of the first and second frame sides may comprise at least one frame aperture extending through the first material, each frame aperture sized large enough to receive a first or a second projection of the at least one projection on each of the first and second carrier sides. The lens assembly may be mounted on the goggle frame, covering at least one lens aperture defined by the goggle frame. The first and second lens retention shelves may be made of a second material harder than the first material and respectively disposed behind the first frame side and the second frame side. The first lens retention shelf may comprise a first strap receptor and at least a first projection connector corresponding to the first projection, the first projection connector aligned with a first frame aperture of the at least one frame aperture and sized to receive and engage the first projection with the goggle frame interposed between the first lens retention shelf and the lens. The second lens retention shelf may comprise a second strap receptor and at least a second projection connector corresponding to the second projection, the second lens retention shelf aligned with a second frame aperture of the at least one frame aperture and sized to receive and engage the second projection with the goggle frame interposed between the second lens retention shelf and the lens. The goggle strap may have a first end and a second end of the goggle strap coupled with the goggle frame through one of the two lens retention shelves.

Particular embodiments may comprise one or more of the following. Each of the first projection connector and the second projection connector may comprise at least one slit across the first or second projection connector. Each of the first and second projection connectors may further comprise a relief cut extending from an edge of the first or second projection connector and has a width greater than a width of the slit. The lens carrier may further comprise at least one of one or more magnets and one or more attractors, and the goggle frame may comprise at least one of one or more corresponding attractors and one or more corresponding magnets. Each of the first and second strap receptors may comprise a strap opening, each of the first and second ends of the goggle strap threaded through the strap opening and disposed on a side of the strap opening opposite a remaining goggle strap. Each of the first and second ends of the goggle strap may comprise a thickened edge having a thickness greater than thickness of an adjacent portion of the goggle strap. The strap opening may comprise a first portion and a second portion, the first portion having a width greater than a width of the second portion and large enough to receive the thickened edge, and the second portion having the width large enough to receive the adjacent portion of the goggle strap but smaller than the thickness of the thickened edge.

According to an aspect of the disclosure, a pair of goggles may comprise a lens assembly, a goggle frame, and at least one lens retention shelf. The lens assembly may include at least one lens and at least one projection disposed on the lens assembly. The goggle frame may comprise a first frame side and be made of a first material, the first frame side comprising at least one frame aperture extending through the first material, each frame aperture sized large enough to receive a first projection of the at least one projection. The lens assembly may be mounted on the goggle frame, covering at least one lens aperture defined by the goggle frame. The at least one lens retention shelf may be made of a second material harder than the first material, a first lens retention shelf of the at least one lens retention shelf disposed behind the first frame side. The first lens retention shelf may comprise at least one first projection connector corresponding to the first projection, the first projection connector aligned with a first frame aperture of the at least one frame aperture and sized to receive and engage the first projection with the goggle frame interposed between the first lens retention shelf and the lens.

Particular embodiments may comprise one or more of the following. The first projection connector may comprise at least one slit across the first projection connector. The first projection connector may further comprise a relief cut extending from an edge of the first projection connector, the relief cut having a width greater than a width of the slit. The lens assembly may comprise at least one of one or more magnets and one or more attractors, and the goggle frame may comprise at least one of one or more corresponding attractors and one or more corresponding magnets. The goggle strap may have a first end coupled with the goggle frame through the first lens retention shelf. The first lens retention shelf may comprise a strap receptor including a strap opening, the first end of the goggle strap threaded through the strap opening and disposed on a side of the strap opening opposite a remaining goggle strap. Each of the first and second ends of the goggle strap may comprise a thickened edge having a thickness greater than an adjacent portion of the goggle strap. The strap opening may comprise a first portion and a second portion, the first portion having a width greater than a width of the second portion and large enough to receive the thickened edge, and the second portion having the width large enough to receive the adjacent portion of the goggle strap but smaller than the thickness of the thickened edge.

According to an aspect of the disclosure, a method of assembling a pair of goggles may comprise providing a lens assembly, a goggle frame, and at least one lens retention shelf. The lens assembly may include at least one lens and at least one projection disposed on the lens assembly. The goggle frame may comprise a first material and a first side comprising at least one frame aperture extending through the first side. The at least one lens retention shelf may be made of a second material harder than the first material and may comprise at least one projection connector sized to receive and engage a first projection of the at least one projection, wherein each frame aperture may be sized large enough to receive the first projection. The method may further comprise aligning the first projection with a first frame aperture of the at least one frame aperture and a first projection connector of the at least one projection connector with the first projection disposed in front of the first frame aperture and the first projection connector disposed behind the first frame aperture. The method may further comprise engaging the first projection in the first projection connector with the goggle frame interposed between a first lens retention shelf of the at least one lens retention shelf and the lens by pushing the first projection through the frame aperture and the first projection connector.

Particular embodiments may comprise one or more of the following. The method of assembling a pair of goggles may further comprise disposing the lens retention shelf behind a first frame side of the goggle frame; and coupling a first end of a goggle strap with the lens retention shelf. Coupling a first end may further comprise threading the first end of the goggle strap through a strap opening of the lens retention shelf. Coupling a first end may further comprise threading a thickened edge at the first end of the goggle strap through a first portion of the strap opening having a width greater than a second portion of the strap opening and large enough to receive the thickened edge.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶ 6. Thus, the use of the words "function," "means" or "step" in the Detailed Description or Description of the Drawings or claims is not intended to somehow indicate a desire to invoke the special provisions of 35 U.S.C. § 112, ¶ 6, to define the invention. To the contrary, if the provisions of 35 U.S.C. § 112, ¶ 6 are sought to be invoked to define the inventions, the claims will specifically and expressly state the exact phrases "means for" or "step for", and will also recite the word "function" (i.e., will state "means for performing the function of [insert function]"), without also reciting in such phrases any structure, material, or acts in support of the function. Thus, even when the claims recite a "means for performing the function of . . . " or "step for performing the function of . . . ," if the claims also recite any structure, material, or acts in support of that means or step, or to perform the recited function, it is the clear intention of the inventors not to invoke the provisions of 35 U.S.C. § 112, ¶6. Moreover, even if the provisions of 35 U.S.C. § 112, ¶6, are invoked to define the claimed aspects, it is intended that these aspects not be limited only to the specific structure, material, or acts that are described in the preferred embodiments, but in addition, include any and all structures, material, or acts that perform the claimed function as described in alternative embodiments or forms in the disclosure, or that are well-known present or later-developed, equivalent structures, material, or acts for performing the claimed function.

The foregoing and other aspects, features, and advantages will be apparent to those artisans of ordinary skill in the art from the DETAILED DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DETAILED DESCRIPTION

While this disclosure includes embodiments in many different forms, they are shown in the drawings and will herein be described in detailed particular embodiments with the understanding that the present disclosure is to be considered as an exemplification of the principles of the disclosed methods and systems, and is not intended to limit the broad aspect of the disclosed concepts to the embodiments illustrated.

The frame of a pair of goggles is desirable to be manufactured from a soft, flexible material, such as plastic or rubber, by injection molding or other molding process known in the art, for comfort and a good fit of the goggles to the wearer's face. When the frame is manufactured of such a soft, flexible material, the connectors from the lens, however, often become loose from the frame because the openings on the frame for the connectors are also soft and flexible and, therefore, lack a sufficient grip on the connectors. This can cause the lens to become detached from the frame at unintended times.

Figure 1A:
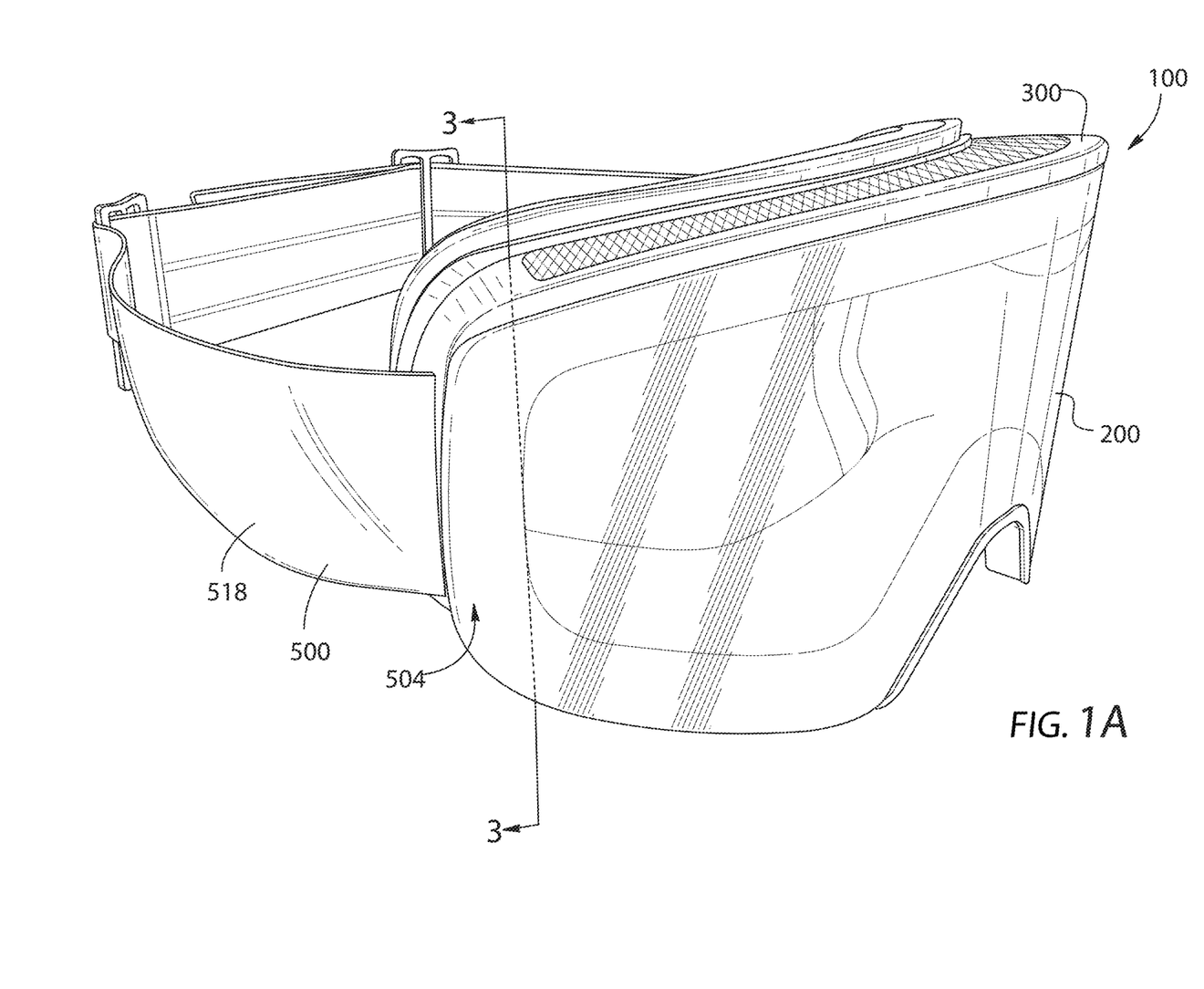
FIG. 1A is a perspective view of a pair of goggles.
Figure 1B:
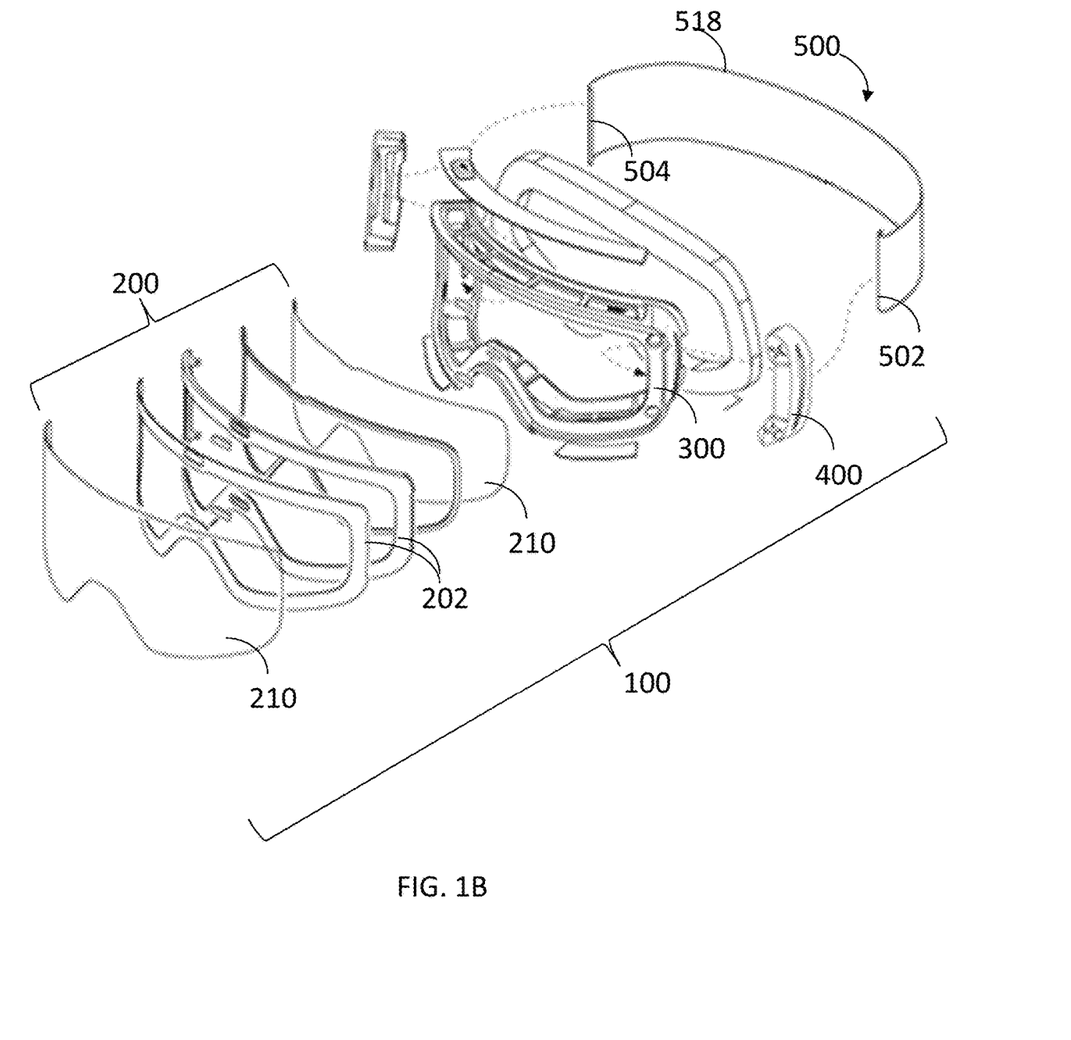
FIG. 1B is an exploded view of the goggles shown in FIG. 1A.
Figure 2:
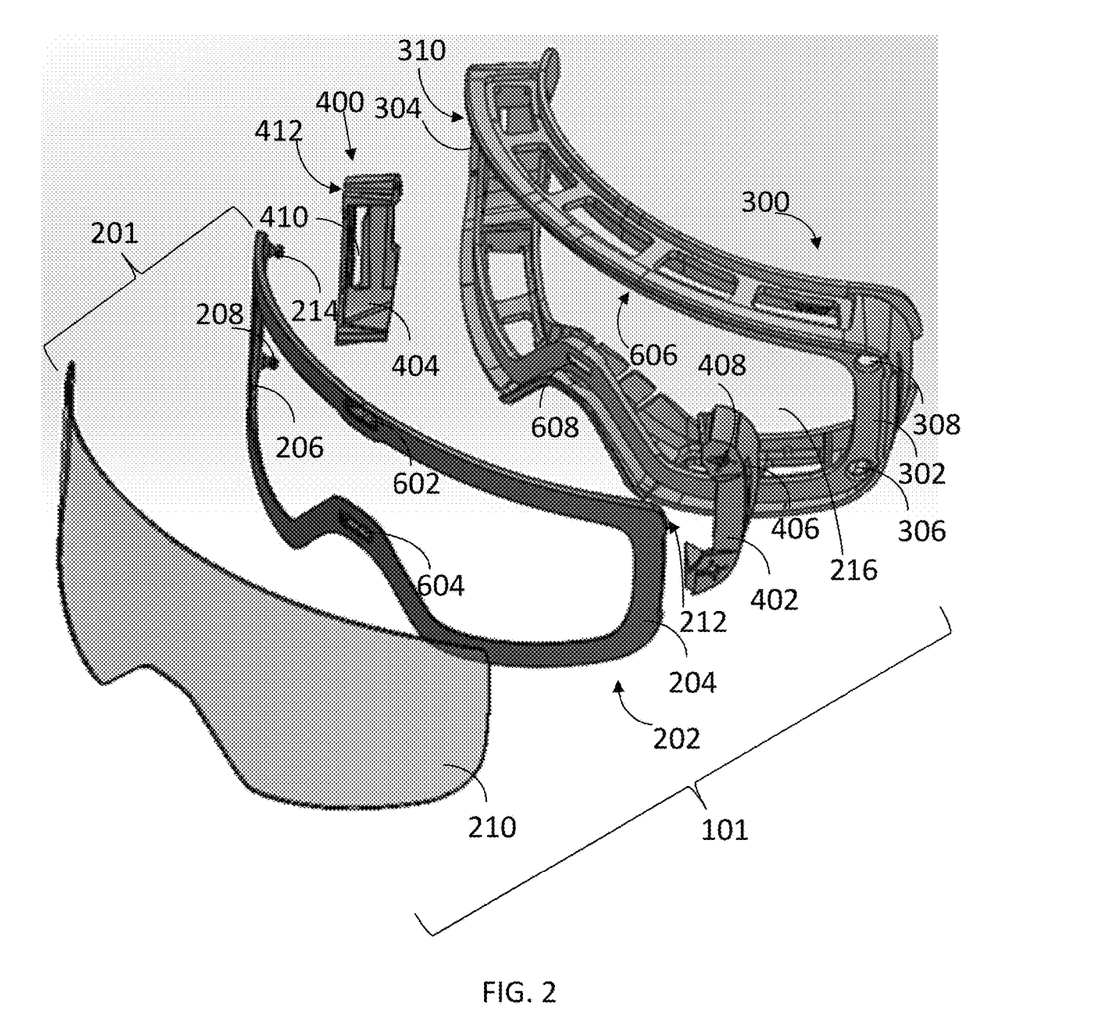
FIG. 2 is an exploded view of another embodiment of goggles.

Contemplated as part of this disclosure is a pair of goggles that can be assembled together through one or more lens retention shelves, where the goggle frame can be made of a flexible material but the connection between the lens assembly and the goggle frame does not become loose because of the flexibleness of the material, as well as a method of assembling a pair of goggles. Goggles 100, 101 comprise a lens assembly 200, 201, a goggle frame 300, and at least one lens retention shelf, lens shelf, or retention shelf 400 (FIGS. 1A-2). FIG. 1A illustrates an example pair of goggles 100; and FIG. 1B shows an exploded view of the goggles 100. In some embodiments, as indicated by the directional arrows extending from the goggle strap or strap 500 to the lens retention shelf 400 and then to the goggle frame 300 in FIG. 1B, when assembled, the goggle strap 500 may be assembled with the lens retention shelf 400 and the lens retention shelf 400 may then sit behind the goggle frame.

Figure 5:
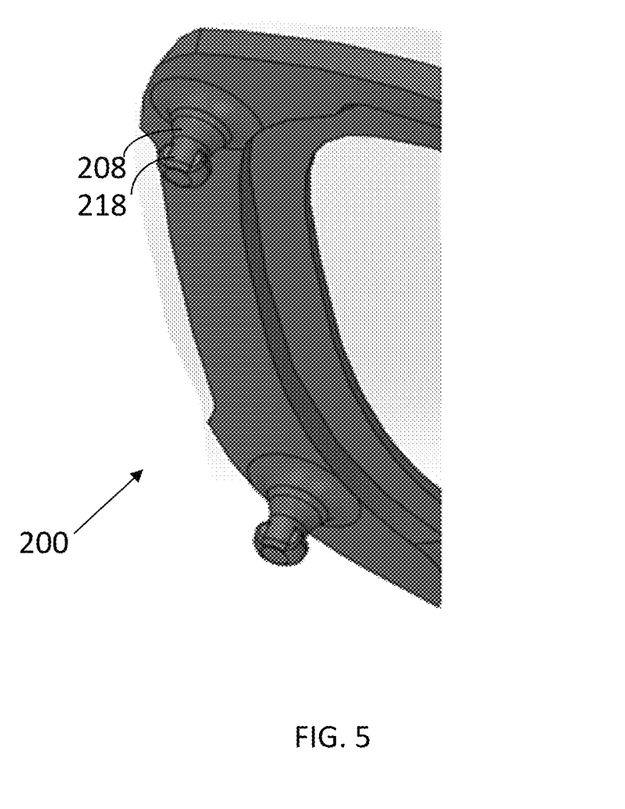
FIG. 5 is a rear perspective view of a part of a lens assembly.

The lens assembly 200 includes at least one lens 210 and at least one projection 208, such as a first projection 212, disposed on the lens assembly 200 (FIGS. 1B and 2). The projection 208 may be disposed at any location on the lens assembly 200. The at least one projection 208 may include a second projection 214. The projection 208 may comprise an enlarged head 218 (FIG. 5) of any shape appropriate to engage the lens retention shelf.

The lens assembly 200 may further comprise at least one lens carrier 202. A lens carrier 202 comprises a first carrier side 204, and a second carrier side 206 opposite the first carrier side 204. The at least one projection 208 may be disposed on each of the first and second carrier sides 204 and 206. The at least one lens 210 may be mounted on the lens carrier 202. In some embodiments, the lens assembly 200 (FIG. 1B) may comprise multiple lenses 210 and multiple lens carriers 202. In some embodiments, the lens assembly 201 (FIG. 2) comprises one lens 210 and one lens carrier 202. In some embodiments, the lens assembly comprises one or more lenses 210 without a lens carrier and with one or more projections disposed on the lenses.

The goggle frame 300 is made of a first material. The goggle frame 300 may comprise a first frame side 302. The first frame side 302 may comprise at least one frame aperture 306, including a first frame aperture 308, extending through the first material. Each frame aperture may be sized large enough to receive a first projection 212 of the at least one projection 208. The lens assembly 200 may be mounted on the goggle frame 300 and cover at least one lens aperture 216 defined by the goggle frame 300.

The goggle frame 300 may further comprise a second frame side 304 opposite the first frame side 302. The second frame side 304 may also comprise at least one frame aperture 306, including a second frame aperture 310, extending through the first material. Each frame aperture 306 may be sized large enough to receive a second projection 214 of the at least one projection 208.

The lens assembly 200, 201 may further comprise one or more magnets 602, one or more attractors 604, or both. The magnets 602 and the attractors 604 may be disposed on the lens carrier 202 or on the lens (not shown). The goggle frame 300 may comprise one or more corresponding attractors 606, one or more corresponding magnets 608, or both such that the magnets and attractors attach to each other and form attachment between the lens assembly 200, 201 and the goggle frame 300. The magnets and attractors may be disposed on any locations on the lens assembly 200, 201. In these or other embodiments, the lens assembly 200, 201 may comprise a manual locator, such as a mechanical interface, protrusion or recess on the goggle frame 300 and a mating mechanical interface 3 on the lens assembly 200, 201, instead of or in addition to attractors, to help position the lens assembly 200, 201 on the goggle frame 300.

Figure 4A:
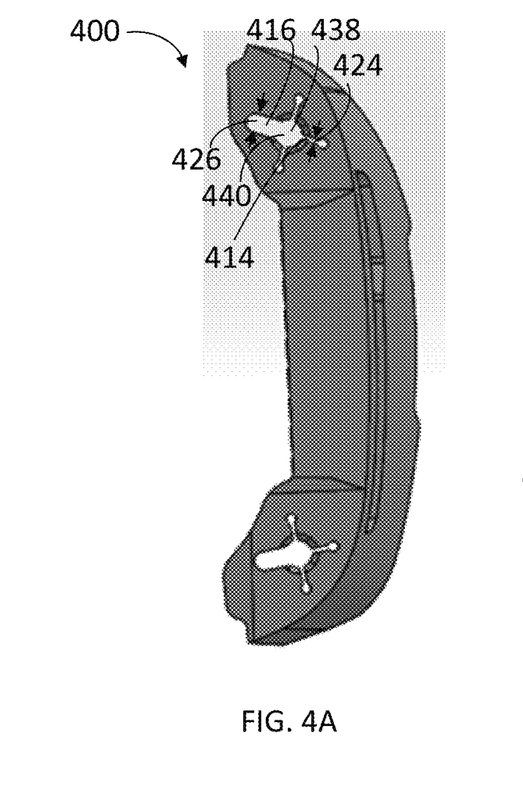
FIG. 4A is a front perspective view of a lens retention shelf.
Figure 4B:
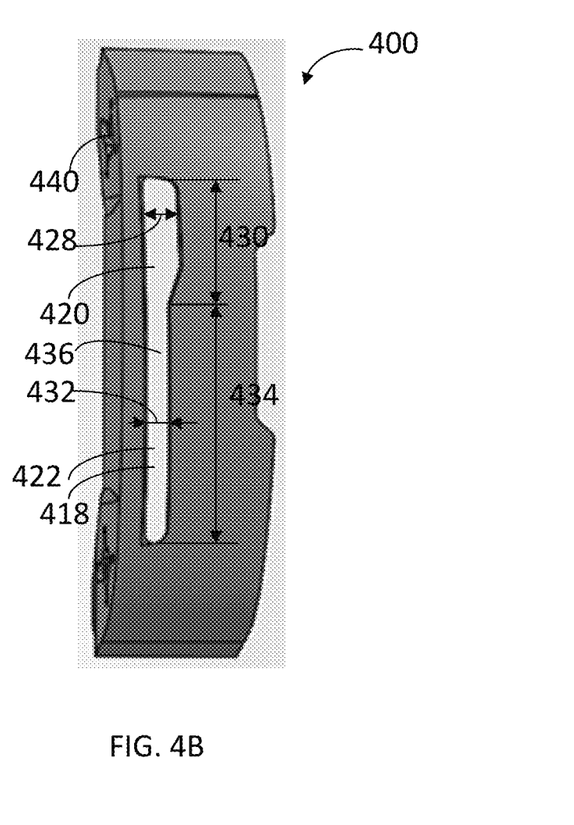
FIG. 4B is a side perspective view of the lens retention shelf shown in FIG. 4A.

The lens retention shelf 400 is made of a second material harder than the first material that the goggle frame is made of. The lens retention shelf 400 comprises one or more projection connectors 440 (FIGS. 4A and 4B). A projection connector 440 may comprise a shelf aperture 438. In some embodiments, the projection connector deflects and the shelf aperture expands when a projection is being pushed through the projection connector and the aperture. When the projection has been pushed through, the projection connector and the aperture resiliently recover to the original state and hold the projection in place. The lens retention shelf 400 may further comprise a strap receptor 436. A first lens retention shelf, a first lens shelf, or a first retention shelf 402 of the at least one lens retention shelf 400 is disposed behind the first frame side 302 of the goggle frame 300. The first lens retention shelf 402 comprises at least a first projection connector 408 corresponding to the first projection 212. The first projection connector 408 is aligned with the first frame aperture 308 of the at least one frame aperture 306 and is sized to receive and engage the first projection 212 with the goggle frame 300 interposed between the first lens retention shelf 400 and the lens 210. The first lens retention shelf 402 may further comprise a first strap receptor 406.

The at least one lens retention shelf 400 may include a second lens retention shelf, a second lens shelf, or a second retention shelf 404. The second lens retention shelf 404 may be disposed behind the second frame side 304 of the goggle frame 300. The second lens retention shelf 404 further comprises at least a second projection connector 412 corresponding to the second projection 214. The second projection connector 412 is aligned with a second frame aperture 308 of the at least one frame aperture 306 and is sized to receive and engage the second projection 214 with the goggle frame 300 interposed between the second lens retention shelf 404 and the lens 210. The second lens retention shelf 404 may further comprise a second strap receptor 410.

By using a material for the lens retention shelf that is harder than the material for the goggle frame, the goggle frame can be made of a soft, pliable, flexible material that is comfortable and fits well on the wearer's face while the lens retention shelf is rigid enough to hold the projection of the lens assembly in place. In some embodiments, a projection connector may be disposed on the lens assembly while projections are disposed on the lens retention shelf so that the projections on the lens retention shelf engages the projection connector on the lens assembly, with the goggle frame interposed between the lens assembly and the lens retention shelf. Use of a harder material for the lens retention shelf, the lens assembly projection connectors make an audible confirming "click" sound when they connect to confirm that the lens is securely attached to the goggle frame. Additionally, use of a lens retention shelf separate from the goggle frame enables easier repair of the goggles and replacement of parts if the lens attachment mechanism breaks. With a separate lens retention shelf insert, if it becomes broken, only that piece need be replace rather than the entire goggle frame.

The projection connector 440 may further comprise at least one slit 414 across the projection connector 440 (FIG. 4A) and a relief cut 416 extending from an edge of the projection connector 440 (FIG. 4A). The relief cut 416 may have a width 426 greater than a width 424 of the slit 414. The relief cut 416 can decrease the force on the projection connector from assembling the projection into the projection connector or dissembling the projection out of the projection connector 440. The relief cut 416, therefore, may help to decrease the potential damage or deformation to the slits, or may otherwise help to limit the projections on the lens assembly from buckling or snapping off, due to the assembling and disassembling. As a result, the life span of the goggles can be extended. In some embodiments, the slits 414 are disposed along a majority of the circumference of the shelf aperture 438 while the relief cut 416 is disposed on a minority of the circumference of the shelf aperture 438 (FIG. 4A). Consequently, the strength of the hold of the projection connector 440 on the projection 214 is maintained while the potential damage to the projection connector 440 or to the projection 214 is limited.

Figure 3:
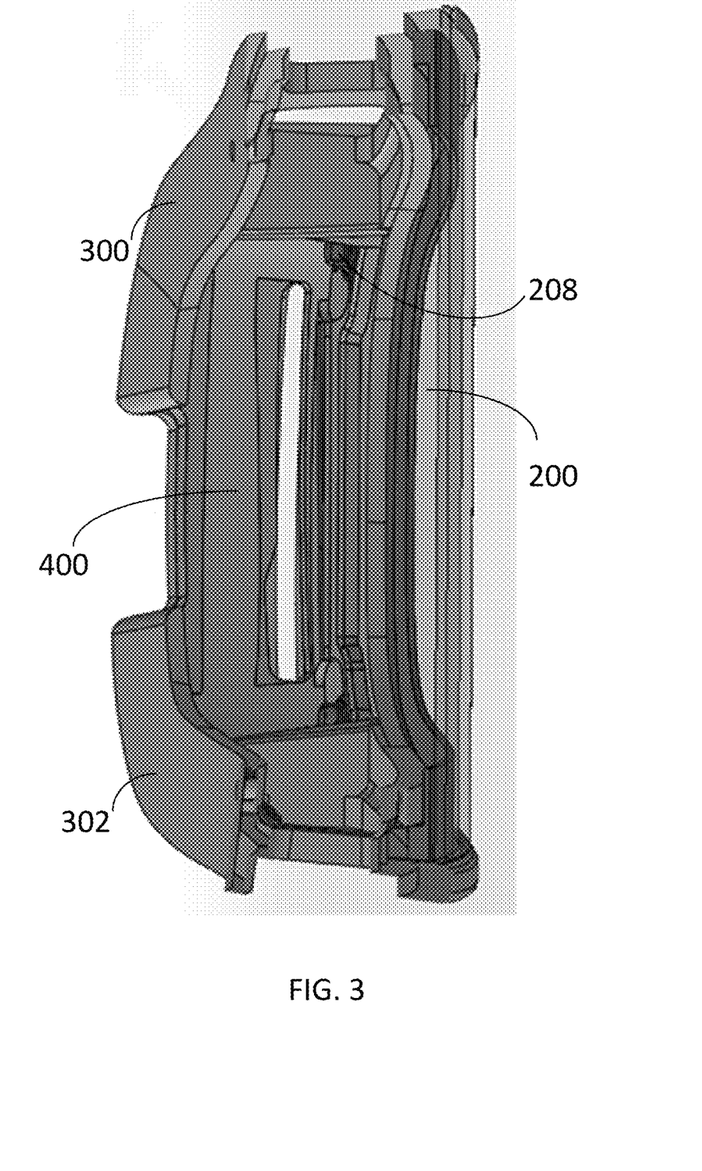
FIG. 3 is a cross-sectional view of the goggles shown in FIG. 1A without the goggle strap, taken along cross-section lines 3-3.

To attach a lens assembly 200 with a goggle frame 300, a lens retention shelf 400 is placed behind the goggle frame 300 by aligning a projection connector 440 of a lens retention shelf 400 behind a frame aperture 306 of the goggle frame 300. Then, a projection 208 of the lens assembly 200, 201 is pushed through both the frame aperture 306 and the projection connector 440, retaining the enlarged end of the projection 208 behind the projection connector 440. For example, FIG. 3 shows a cross-sectional view of goggles, where a lens assembly 200 is assembled onto a goggle frame 300 through a lens retention shelf 400. The goggle frame 300 is interposed between the lens assembly 200 and the lens retention shelf 400, where the projection 208 of the lens assembly 200 is disposed behind the lens retention shelf 400. Although the lens retention shelf 400 in FIG. 3 is shown to extend a majority of a first frame side 302 of the goggle frame 300, the lens retention shelf may be smaller. This allows the increase of the flexibility of the goggle frame and the comfort on the wearer's face. For the illustrative purpose, FIG. 3 shows the lens retention shelf 400 is disposed at a first frame side 302. The lens retention shelf may be disposed at other parts or locations of the goggle frame as long as the lens assembly comprises one or more projections at corresponding parts or locations of the lens assembly. Further, although the lens retention shelf 400 is shown having two projection connectors in FIG. 3, a lens retention shelf may comprise one, three, four or any other number of projection connectors. The number of lens retention shelves on a pair of goggles is not limited to two as depicted in FIGS. 1B and 2, either. Assembled goggles may comprise one, three, or any number of lens retention shelves.

A goggle strap 500 may couple to a goggle frame 300 through a lens retention shelf 400. In some embodiments, a goggle strap 500 is assembled onto a goggle frame 300 through one of the two lens retention shelves 402 and 404. In other embodiments, the goggle strap may couple to the goggle frame through another way known in the art that does not involve a lens retention shelf. A goggle strap 500 has a first end 502 and a second end 504. When a lens retention shelf 400 is used to receive the goggle strap 500, the strap receptor 436 of the lens retention shelf 400 may be configured to receive either the first end 502 or the second end 504 and includes a strap opening 418. Each of the first and second ends 502 and 504 of the goggle strap 500 are threaded through a respective strap opening 418 and be disposed on a side of the strap opening 418 opposite a remaining goggle strap 518. The goggle strap 500 may be attached to the goggle frame 300 and lens retention shelf 400 through other mechanisms known in the art. For example, the goggle strap 500 may comprise a strap buckle (not shown) at an end of the goggle strap, and the strap receptor may comprise a mating buckle receiver that receives and couples with the strap buckle. In another example, a strap post or a strap "bone" may be included at the end of the goggle strap. The strap is sewn around the post and, during assembly, the strap post is threaded through the opening in the strap shelf and then turned so that the strap post not parallel to the strap opening to restrict the strap from falling back through the opening by the interference between the strap post and the lens retention shelf.

Figure 6A:
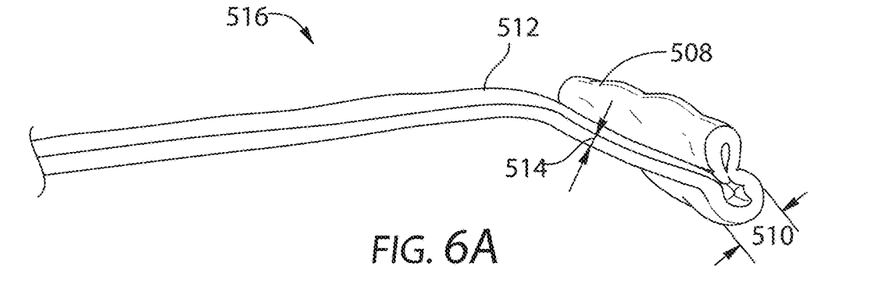
FIG. 6A is a side view of a part of a goggle strap.
Figure 6B:
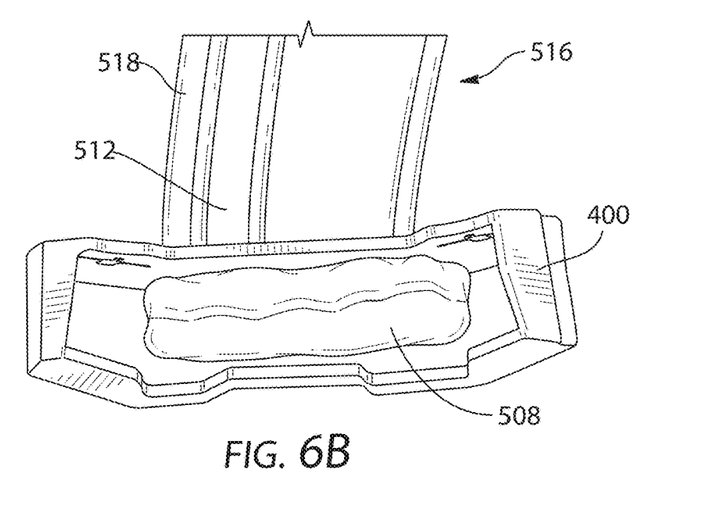
FIG. 6B is a bottom view of the part of goggle strap shown in FIG. 6A assembled into a lens retention shelf.
Figure 6C:
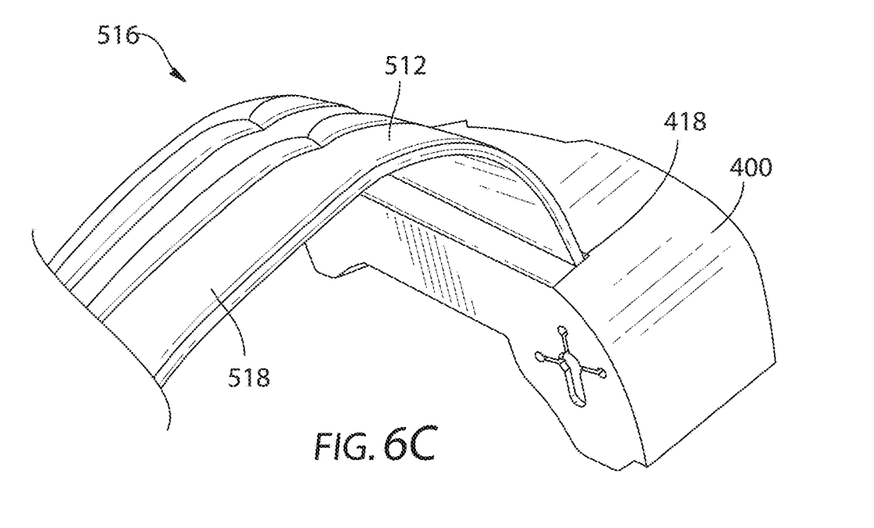
FIG. 6C is a top perspective view of the part of goggle strap and the lens retention shelf shown in FIG. 6B.

In some embodiments, the first end 502 of the goggle strap 500 may further comprise a thickened edge 508 (FIGS. 6A-6C). The second end 504 of the goggle strap 500 may also comprise a thickened edge 508. The thickened edge 508 may be constructed by folding the end 516 of the goggle strap 500 into a multi-layered fold and holding the fold in place by sewing, gluing, stitching, or other mechanisms. The thickened edge may also be constructed by attaching an additional layer or object at the end of the goggle strap. The thickness 510 of the edge 508 is greater than the thickness 514 of the portion 512 of the goggle strap that is adjacent to the edge 508 (FIG. 6A).

In some embodiments, the strap opening 418 may comprise a first portion 420 and a second portion 422 (FIG. 4B). The first portion 420 may have a width 428 greater than a width 432 of the second portion 422 and large enough to receive the edge 508. The width 432 of the second portion 422 is large enough to receive the adjacent portion 512 of the goggle strap 500 but smaller than the thickness 510 of the edge 508. In some embodiments, the length 430 of the first portion 420 is smaller than the length 434 of the second portion 422. To attach the goggle strap 500 having a thickened edge 508 to the lens retention shelf 400, the thickened edge 508 can be threaded through the first portion 420. Once the entire thickened edge 508 is threaded through the first portion 420 and disposed on the side of the lens retention shelf 400 opposite the remaining goggle strap 518, the adjacent portion 512 of the goggle strap 500 may be spread along the strap opening 418. Because the width 432 of the second portion 422 is smaller than the thickness 510 of the edge 508, or the thickness of the edge is folded back on itself with the edge extending from the strap, the edge 508 is restrained from being slipped out of the strap opening 418.

Figure 7:
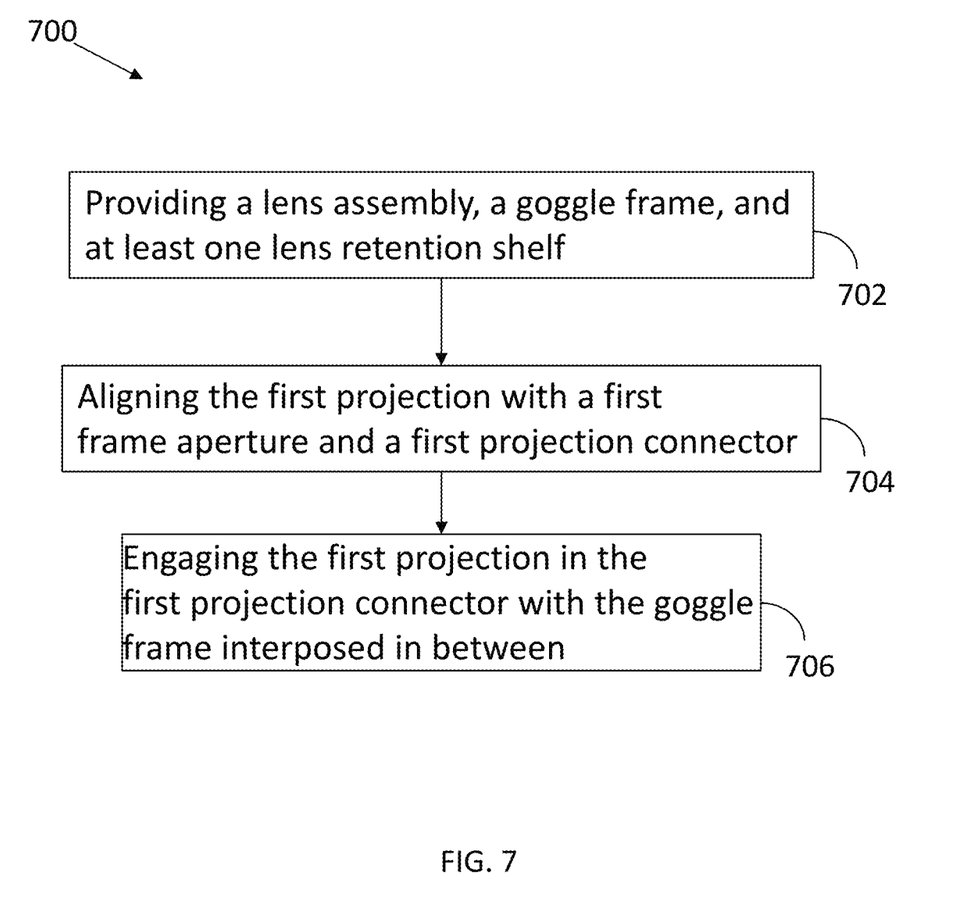
FIG. 7 is a flow chart of a method of assembling a pair of goggles.

Methods of assembling a pair of goggles are also provided herein. FIG. 7 illustrates an example method of assembling a pair of goggles (700). The method (700) comprises providing a lens assembly, a goggle frame, and at least one lens retention shelf (702). The lens assembly includes at least one lens and at least one projection disposed on the lens assembly. The goggle frame comprises a first material and a first side comprising at least one frame aperture extending through the first side. The at least one lens retention shelf is made of a second material harder than the first material and comprises at least one projection connector sized to receive and engage a first projection of the at least one projection. Each frame aperture is sized large enough to receive the first projection.

The method (700) further comprises aligning the first projection with a first frame aperture of the at least one frame aperture and a first projection connector of the at least one projection connector with the first projection disposed in front of the first frame aperture and the first projection connector disposed behind the first frame aperture (704). The method (700) further comprises engaging the first projection in the first projection connector with the goggle frame interposed between the first lens retention shelf and the lens by pushing the first projection through the frame aperture and the projection connector (706).

The method (700) may further comprise disposing the lens retention shelf behind a first frame side of the goggle frame, and coupling a first end of a goggle strap with the lens retention shelf. Coupling the first end may further comprise threading the first end of the goggle strap through a strap opening of the lens retention shelf. Coupling the first end may further comprise threading a thickened edge at the first end of the goggle strap through a first portion of the strap opening that has a width greater than the width of a second portion of the strap opening and large enough to receive the edge.

This disclosure, its aspects and implementations, are not limited to the specific components or assembly procedures disclosed herein. Many additional components and assembly procedures known in the art consistent with the goggle assemblies, and methods of assembling a pair of goggles will become apparent for use with implementations of the apparatus and methods in this disclosure. In places where the description above refers to particular implementations of goggle assemblies, it should be readily apparent that a number of modifications may be made without departing from the spirit thereof and that these implementations may be applied to other goggle assemblies. The presently disclosed implementations are, therefore, to be considered in all respects as illustrative and not restrictive, the scope of the disclosure being indicated by the appended claims rather than the foregoing description. All changes that come within the meaning of and range of equivalency of the description are intended to be embraced therein. Accordingly, for example, although particular goggle assemblies and methods of assembling a pair of goggles are disclosed, such apparatus, methods, and implementing components may comprise any shape, size, style, type, model, version, class, grade, measurement, concentration, material, quantity, the like as is known in the art for such apparatus, methods, and implementing components, and/or the like consistent with the intended operation of the goggle assemblies, and methods of assembling a pair of goggles may be used.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

The invention claimed is:

1. A pair of goggles comprising:
a lens assembly including:
at least one lens carrier comprising a first carrier side, a second carrier side opposite the first carrier side, and at least one projection extending rearward from each of the first and second carrier sides; and
at least one lens mounted on the lens carrier;
a goggle frame comprising a first frame side and a second frame side opposite the first frame side, the goggle frame comprising a first pliable material and each of the first and second frame sides comprising at least one frame aperture extending through the first pliable material, each frame aperture sized large enough to receive a first or a second projection of the at least one projection on each of the first and second carrier sides, the lens assembly mounted on the goggle frame and covering at least one lens aperture defined by the goggle frame;
first and second lens retention shelves made of a second rigid material harder than the first pliable material and respectively disposed behind the first frame side and the second frame side, the first lens retention shelf comprising a first strap receptor and at least a first projection connector corresponding to the first projection, the first projection connector aligned with a first frame aperture of the at least one frame aperture and sized to receive and engage the first projection with the goggle frame interposed between the first lens retention shelf and the lens, the second lens retention shelf comprising a second strap receptor and at least a second projection connector corresponding to the second projection, the second lens retention shelf aligned with a second frame aperture of the at least one frame aperture and sized to receive and engage the second projection with the goggle frame interposed between the second lens retention shelf and the lens; and
a goggle strap having a first end and a second end of the goggle strap coupled with the goggle frame through one of the two lens retention shelves.

2. The goggles of claim 1, wherein each of the first projection connector and the second projection connector comprises at least one slit across the first or second projection connector.

3. The goggles of claim 2, wherein the each of the first and second projection connectors further comprises a relief cut extending from an edge of the first or second projection connector and has a width greater than a width of the slit.

4. The goggles of claim 1, wherein the lens carrier further comprises at least one of one or more magnets and one or more attractors, and the goggle frame comprises at least one of one or more corresponding attractors and one or more corresponding magnets.

5. The goggles of claim 1, wherein each of the first and second strap receptors comprises a strap opening, each of the first and second ends of the goggle strap threaded through the strap opening and disposed on a side of the strap opening opposite a remaining goggle strap.

6. The goggles of claim 5, wherein each of the first and second ends of the goggle strap comprises a thickened edge having a thickness greater than thickness of an adjacent portion of the goggle strap.

7. The goggles of claim 6, wherein the strap opening comprises a first portion and a second portion, the first portion having a width greater than a width of the second portion and large enough to receive the thickened edge, and the second portion having the width large enough to receive the adjacent portion of the goggle strap but smaller than the thickness of the thickened edge.

8. A pair of goggles comprising:
a lens assembly including at least one lens and at least one projection extending rearward from the lens assembly;
a goggle frame comprising a first frame side and made of a first pliable material, the first frame side comprising at least one frame aperture extending through the first pliable material, each frame aperture sized large enough to receive a first projection of the at least one projection, the lens assembly mounted on the goggle frame and covering at least one lens aperture defined by the goggle frame; and
at least one lens retention shelf made of a second rigid material harder than the first pliable material, a first lens retention shelf of the at least one lens retention shelf disposed behind the first frame side, the first lens retention shelf comprising at least one first projection connector corresponding to the first projection, the first projection connector aligned with a first frame aperture of the at least one frame aperture and sized to receive and engage the first projection with the goggle frame interposed between the first lens retention shelf and the lens.

9. The goggles of claim 8, wherein the first projection connector comprises at least one slit across the first projection connector.

10. The goggles of claim 9, wherein the first projection connector further comprises a relief cut extending from an edge of the first projection connector, the relief cut having a width greater than a width of the slit.

11. The goggles of claim 8, wherein the lens assembly comprises at least one of one or more magnets and one or more attractors, and the goggle frame comprises at least one of one or more corresponding attractors and one or more corresponding magnets.

12. The goggles of claim 8, further comprising a goggle strap, wherein the goggle strap having a first end coupled with the goggle frame through the first lens retention shelf.

13. The goggles of claim 12, wherein the first lens retention shelf comprises a strap receptor including a strap opening, the first end of the goggle strap threaded through the strap opening and disposed on a side of the strap opening opposite a remaining goggle strap.

14. The goggles of claim 13, wherein each of the first and second ends of the goggle strap comprises a thickened edge having a thickness greater than an adjacent portion of the goggle strap.

15. The goggles of claim 14, wherein the strap opening comprises a first portion and a second portion, the first portion having a width greater than a width of the second portion and large enough to receive the thickened edge, and the second portion having the width large enough to receive the adjacent portion of the goggle strap but smaller than the thickness of the thickened edge.

16. A method of assembling a pair of goggles comprising:
providing a lens assembly including at least one lens and at least one projection extending from the lens assembly, a goggle frame comprising a first pliable material and a first side comprising at least one frame aperture extending through the first side, and at least one lens retention shelf made of a second rigid material harder than the first pliable material and comprising at least one projection connector sized to receive and engage a first projection of the at least one projection, wherein each frame aperture is sized large enough to receive the first projection;
aligning the first projection with a first frame aperture of the at least one frame aperture and a first projection connector of the at least one projection connector with the first projection disposed in front of the first frame aperture and the first projection connector disposed behind the first frame aperture; and
engaging the first projection in the first projection connector with the goggle frame interposed between a first lens retention shelf of the at least one lens retention shelf and the lens by pushing the first projection through the frame aperture and the first projection connector.

17. The method of claim 16, further comprising:
disposing the lens retention shelf behind a first frame side of the goggle frame; and
coupling a first end of a goggle strap with the lens retention shelf.

18. The method of claim 17, wherein coupling a first end further comprises threading the first end of the goggle strap through a strap opening of the lens retention shelf.

19. The method of claim 18, wherein coupling a first end further comprises threading a thickened edge at the first end of the goggle strap through a first portion of the strap opening having a width greater than a second portion of the strap opening and large enough to receive the thickened edge.

* * * * *